(12) United States Patent
Zacharias (10) Patent No.: US 8,721,594 B2
(45) Date of Patent: May 13, 2014

(54) POST-OCCLUSION CHAMBER COLLAPSE CANCELING SYSTEM FOR A SURGICAL APPARATUS AND METHOD OF USE

(75) Inventor: Jaime Zacharias, Santiago (CL)

(73) Assignee: Alcon Research, Ltd., Fort Worth, TX (US)

( * ) Notice: Subject to any disclaimer, the term of this patent is extended or adjusted under 35 U.S.C. 154(b) by 434 days.

(21) Appl. No.: 11/765,223

(22) Filed: Jun. 19, 2007

(65) Prior Publication Data

US 2008/0319374 A1   Dec. 25, 2008

(51) Int. Cl.
*A61M 1/00* (2006.01)
*A61M 31/00* (2006.01)

(52) U.S. Cl.
USPC ............ 604/119; 604/31; 604/35; 604/67

(58) Field of Classification Search
USPC ......... 604/22, 27, 28, 30, 31, 35, 43, 119, 65, 604/67
See application file for complete search history.

(56) References Cited

U.S. PATENT DOCUMENTS

| | | | |
|---|---|---|---|
| 3,902,495 A | | 9/1975 | Weiss et al. |
| 4,496,342 A | * | 1/1985 | Banko ............................ 604/27 |
| 4,559,045 A | * | 12/1985 | Danby et al. .................. 604/250 |
| 5,106,367 A | * | 4/1992 | Ureche et al. ................... 604/30 |
| 5,167,620 A | | 12/1992 | Ureche et al. |
| 5,267,956 A | | 12/1993 | Beuchat |
| 5,429,601 A | | 7/1995 | Conley et al. |
| 5,569,188 A | * | 10/1996 | Mackool ......................... 604/67 |
| 5,591,127 A | * | 1/1997 | Barwick et al. ................. 604/66 |
| 5,697,898 A | * | 12/1997 | Devine ............................ 604/22 |
| 5,700,240 A | | 12/1997 | Berwick, Jr. et al. |
| 5,725,495 A | * | 3/1998 | Strukel et al. ................... 604/44 |
| 5,733,256 A | * | 3/1998 | Costin ............................. 604/22 |
| 6,241,700 B1 | * | 6/2001 | Leukanech ...................... 604/19 |
| 6,599,271 B1 | * | 7/2003 | Easley ........................... 604/119 |
| 2004/0039351 A1 | * | 2/2004 | Barrett .......................... 604/272 |
| 2004/0077993 A1 | * | 4/2004 | Cionni ............................ 604/31 |
| 2004/0253129 A1 | | 12/2004 | Sorensen |
| 2005/0070871 A1 | * | 3/2005 | Lawton et al. ................ 604/403 |
| 2005/0209560 A1 | * | 9/2005 | Boukhny et al. ............. 604/118 |
| 2005/0245886 A1 | * | 11/2005 | Devine et al. ................. 604/264 |
| 2005/0261628 A1 | * | 11/2005 | Boukhny et al. ............. 604/118 |
| 2005/0267504 A1 | * | 12/2005 | Boukhny et al. ............. 606/171 |
| 2006/0078448 A1 | * | 4/2006 | Holden ....................... 417/477.2 |
| 2006/0224107 A1 | * | 10/2006 | Claus et al. .................... 604/44 |

(Continued)

FOREIGN PATENT DOCUMENTS

WO   WO03030717 A2   3/2005

OTHER PUBLICATIONS

Jaime Zacharias, Post-Occlusion Surge: An Ongoing Challenge, Symposium American Society of Cataract and Refractive Surgeons Anual Meeting Apr. 28-May 2, 2001 , San Diego, CA, USA. Film Festival Award, Runner-Up Category Instruments and Devices.

(Continued)

*Primary Examiner* — Kevin C Sirmons
*Assistant Examiner* — William Carpenter
(74) *Attorney, Agent, or Firm* — Kenneth D. Bassinger (57) ABSTRACT

A post-occlusion chamber collapse canceling system for a surgical apparatus that detects the breaking of occlusions by tissue fragments in the distal end of the aspiration path and produces a response consisting in a transitory blockage of the distal end the aspiration path to terminate the chamber collapse and a transitory venting of the aspiration line to relieve the vacuum, in a way that post-occlusion chamber collapses are cancelled.

11 Claims, 10 Drawing Sheets

(56) References Cited

U.S. PATENT DOCUMENTS

2006/0224143 A1* 10/2006 Claus et al. .................. 604/521
2006/0224163 A1   10/2006 Sutton

OTHER PUBLICATIONS

Jaime Zacharias, Post-Occlusion Surge: An Ongoing Challenge, Symposium American Society of Cataract and Refractive Surgeons Anual Meeting Apr. 28-May 2, 2001, San Diego, CA, USA. Free Paper Presentations, Instruments and Devices, Book of Abstracts.
ASCRS 2001 Awarded Film Uploaded At the Web At www.youtube.com—Post-Occlusion Surge: An Ongoing Challenge URL: http://www.youtube.com/watch?v=QsXFHbEYDd8.
ASCRS 2001 Awarded Film Uploaded At the Web At www.youtube.com—Post-Occlusion Surge: An Ongoing Challenge (Fragment) URL: http://www.youtube.com/watch?v=los521C4O20.

* cited by examiner

PRIOR ART

POST-OCCLUSION CHAMBER COLLAPSE CANCELING SYSTEM FOR A SURGICAL APPARATUS AND METHOD OF USE

BACKGROUND OF THE INVENTION

This invention generally relates to the field of surgery inside a collapsible body chamber and more particularly to a lens removing surgical apparatus.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

Optical aberrations such as myopia, hyperopia, astigmatism and presbiopia can also be corrected by the removal of the natural lens of the eye and the implantation of suitable IOL in a procedure known as refractive lens exchange identical to the cataract surgery procedure, except for the fact that the lens material is usually easier to remove. The best current standard of care procedure to remove cataractous lenses or perform a refractive lens exchange is a surgical technique called phacoemulsification. During this procedure, a hollow phacoemulsification probe is inserted into the eye though a small incision. The tip of the probe is placed in contact with the lens material and the tip is vibrated ultrasonically. The vibrating probe tip liquefies or emulsifies the lens material so that the lens content may be aspirated out of the eye. The lens content, once removed, is replaced by an artificial lens preferably placed inside the lens capsule bag.

A typical phacoemulsification surgical device suitable for ophthalmic procedures consists of an ultrasonically driven hand piece, an attached hollow lensectomy probe, a surrounding coaxial irrigating sleeve and a control console. The hand piece assembly is attached to the control console by electric cables and by flexible irrigation and aspiration tubing. Through the electric cables, the control console provides power to the actuator in the hand piece that is transmitted to the attached lensectomy probe. The flexible tubing supply irrigation fluid to and draw aspiration fluid from the eye through the hand piece assembly. Alternative methods for lens fragmentation currently available consider sonic wave, water-jet and laser powered lens disrupting hand pieces. The irrigation and aspiration systems of these alternative lens removing methods typically operate similarly to standard ultrasonic phacoemulsification.

The operative part of ultrasonic hand pieces is a centrally located, hollow resonating bar or horn directly attached to a set of piezoelectric crystals. The crystals supply the required ultrasonic vibration needed to drive both the horn and the attached probe during phacoemulsification and are controlled by the console. The crystal/horn assembly is suspended within the hollow body or shell of the hand piece by flexible mountings. The hand piece body terminates in a reduced diameter portion or nosecone at the body's distal end. The nosecone is externally threaded to accept the irrigation sleeve. Likewise, the horn bore is internally threaded at its distal end to receive the external threads of the probe. The irrigation sleeve also has an internally threaded bore that is screwed onto the external threads of the nosecone. The hollow probe is adjusted so that the probe tip projects only a predetermined amount past the open end of the irrigating sleeve. Ultrasonic hand pieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the distal end of the lensectomy probe and irrigating sleeve are inserted into a small incision of predetermined width in the cornea, sclera, or other location. The probe tip is ultrasonically vibrated within the irrigating sleeve by the crystal-driven ultrasonic horn, thereby emulsifying the selected tissue in situ. Axis of vibration of the probe tip can be longitudinal, torsional or a combination. One of the advantages of the torsional system is reduced heat generation at wound level with reduced risk of incision thermal injury. The hollow bore of the probe communicates with the bore in the horn that in turn communicates to an aspirate out port in the hand piece. A reduced pressure or vacuum source in the console draws or aspirates the emulsified tissue from the eye through the probe and horn bores and the flexible aspiration line and into a collection device.

The aspiration of emulsified tissue is aided by a flushing solution or irrigant that enters into the surgical site through the small annular gap between the inside surface of the irrigating sleeve and the outer surface of the probe. The flushing solution is typically a saline solution and enters the surgical site with a positive pressure created gravitationally or by forced infusion means, such as an adjustable pressurized gas source. Typical irrigation pressures are set between 40 and 130 cmH2O. The preferred surgical technique is to make the incision into the anterior chamber of the eye as small as possible in order to reduce the risk of induced astigmatism. Up to date these small incisions have had typical widths between 3.5 and 1.8 mm and result in very tight wounds that squeeze the coaxial irrigating sleeve tightly against the lensectomy probe. Friction between the coaxial irrigating sleeve and a vibrating probe generates heat, and probe overheating causing a burn to the tissue is avoided by the cooling effect of the aspirated fluid flowing inside the probe. Occasionally the probe tip becomes occluded with tissue reducing circulation of the cooling aspirate and allowing the probe to build up heat with the risk of thermally damaging the incision.

An alternative technique called Micro Incision Cataract Surgery (MICS) has become popular as it allows further reductions of the incision dimensions. The main aspect of this technique is that the irrigant is no longer delivered into the eye through a coaxial irrigating sleeve located surrounding the lens disrupting hollow probe. With MICS a second irrigating instrument delivers the irrigant solution into the eye through a second small incision. The bare phacoemulsification probe is introduced without any surrounding sleeve through a tight, low leakage, micro-incision having a width in the range of 0.8 to 1.5 mm. The separate irrigating instrument is introduced through another incision having similar characteristics and dimensions. In this way, the MICS technique delivers the irrigant through a hollow instrument inserted into the eye through a second micro-incision. Aspiration of lens fragments and irrigant solution takes place through the aspiration channel of the hollow vibratory probe. The increasingly small incisions currently used in the micro coaxial phacoemulsification technique as well as in the MICS technique limit the flow of irrigant into the eye determining the use of low aspirate flow rates to avoid a negative fluidic balance that can progressively collapse the eye.

When fragments of cataractous tissue occlude the tip of the lensectomy probe, the aspiration pump remains operating and builds a vacuum in the aspiration line. This occlusion typically clears by the action of the built up vacuum aided by vibration of the lensectomy probe. An unwanted phenomenon known as post occlusion surge can occur when the occlusion clears. This phenomenon results in a transient collapse of the anterior chamber of the eye typically lasting fractions of a second. Post occlusion surge creates unstable surgical conditions such as anterior chamber shallowing, pupil contraction and corneal instability, all events that can lead to serious complications such as posterior capsule rupture, vitreous loss and lens luxation. The events that lead to chamber instability are as follows: When the tip of the lensectomy probe becomes occluded by lens fragments, the vacuum that builds up inside the aspiration line contracts the walls of the elastic aspiration tubing. Also, the built up vacuum expands eventual bubbles circulating in the aspirate fluid. These two phenomena add up a volume void. Once the occlusion becomes cleared, the gradient between the positive pressure inside the eye chamber and the negative pressure inside the aspiration line determines a fast inrush of liquid circulating from within the eye chamber toward the aspiration line through the now cleared aspiration probe. This inrush ends after the contracted tubing walls re-expand and the expanded bubbles are collapse due to the dropping vacuum. This inrush of liquid may exceed the rate of infusion of irrigant into the eye leading to a transient chamber collapse. As a mode of example, an occlusion-break occurring at a vacuum level of 500 mmHg can produce a transient inrush of fluid at a flow rate above 80 ml/min during a fraction of a second. A transient chamber collapse will occur until the irrigation solution refills the eye chamber and dynamic fluidic equilibrium is restored.

Several strategies have been implemented to attempt diminish the chamber collapse that results from the post occlusion surge phenomenon. To mention some, a) reduction of the maximum allowed vacuum level in the aspiration line, b) increase in the pressure of the irrigant solution, c) prevention of total occlusion by the incorporation of a small bypass port at the sidewall of the lensectomy probe, d) use of aspiration line tubing made from flexible but non-contracting polymers, e) use of high bore tubing in the irrigation line, f) splitting of the irrigation tubing to infuse the irrigant through two incisions, g) use of a particle retainer filter flowed by a narrow fluid passage in the aspiration line (Cruise Control System, Staar, USA), h) predicting that an occlusion-break will occur after a preset interval of occlusion (vacuum rise) and reversing operation of the aspiration pump to set a lower vacuum level before the occlusion actually breaks (CASE enabled, WhiteStar Signature System, AMO, USA). The method of increasing the pressure of irrigant solution delivered by an irrigation probe may indeed help to attenuate the magnitude of post occlusion-break chamber collapses. However there is concern about using techniques that increase the irrigant pressure to reduce the post occlusion surge phenomenon because of the risks of chamber instability, pupillary dilatation and contraction, ocular pain, hydration of the vitreous, optic nerve damage, herniated iris and others. Active infusion methods that pressurize the irrigant have been proposed but have the added risk of creating an overpressure inside the eye leading to serious complications.

Although the aforementioned techniques may help to reduce the problems associated with the post occlusion surge phenomenon, the increasingly popular tendency to reduce the size of the incisions makes all these measures less effective. In fact post occlusion surge is still a limiting factor to perform a more efficient lensectomy procedure, for example using higher vacuum levels what would allow removal of the lens using lower amounts of lens disrupting energy such as ultrasound, in less time, with lower amounts of irrigant solution.

From a medical standpoint, it would be ideal to perform a lensectomy procedure using the lowest amounts of irrigant solution and the lowest amount of lens disrupting energy. Both, irrigant solution circulation and lens disrupting energy are known to produce surgically induced trauma, such as endothelial cell loss. Therefore, a need continues to exist for an effective post-occlusion chamber collapse canceling system for lens removing surgical apparatus, especially to perform micro-incision cataract surgery.

BRIEF SUMMARY OF THE INVENTION

The present invention improves upon the prior art by providing an post-occlusion chamber collapse canceling system for a surgical apparatus including a control system that prevents the anterior chamber instability associated with the phenomenon of post occlusion surge. This capability is achieved by detecting the occlusion-break events and by a) activating a transitory actuator mediated occlusion in the aspiration line, preferably in proximity to the hand piece, and b) activating a transitory actuator mediated vacuum relieving action. The vacuum relieving action can be in the form of a venting operation, reverse operation of the aspiration pump or other means for vacuum cancellation in the aspiration line. The incorporation of this control system in a surgical apparatus virtually eliminates the instability of the anterior chamber that results from post occlusion surges.

This system allows an operator to safely perform lens exchange procedures through very small incisions using low aspiration flow rates, high vacuum limit levels and low irrigant pressure levels, all factors that reduce surgical trauma. During the period in which the actuator mediated aspiration line blockage is active, lens disrupting energy delivered to the lensectomy probe can be adjusted in a direction that prevents thermal injuries related to poor probe cooling due to blocked outflow. Micro-coaxial phacoemulsification probes, bimanual micro-incision lensectomy probes, laser phacolysis probes, water jet based liquefracture probes, vitrectomy probes and other kinds of irrigation/aspiration probes used during eye surgery may all benefit from this invention.

Accordingly, one objective of the present invention is to provide a post-occlusion chamber collapse canceling system for a surgical apparatus that maintains a stable anterior chamber after occlusion-break events while using high vacuum levels together with small incisions.

It is another objective of the present invention to provide a post-occlusion chamber collapse canceling system for a surgical apparatus to perform cataract surgery that allows reducing tissue disruptive energy such as ultrasound, liquefracture energy and laser energy.

It is another objective of the present invention to provide a post-occlusion chamber collapse canceling system for a surgical apparatus to perform cataract surgery with reduced amounts of irrigant solution.

It is another objective of the present invention to provide a post-occlusion chamber collapse canceling system for a surgical apparatus that allows performing cataract surgery using low infusion pressure with improved eye chamber stability.

It is still another objective of the present invention to provide a post-occlusion chamber collapse canceling system for a surgical apparatus that allows performing perform cataract surgery more efficiently reducing the operative time.

These and other advantages and objectives of the present invention will become apparent from the detailed description and claims that follow.

FIGURE LEYENDS 10 prior art lensectomy surgical system,
11 console,
12 hand piece,
14 lensectomy probe,
16 infusion probe,
18 infusion line,
20 infusion source,
21 aspiration line distal connector
22 aspiration line,
23 aspiration path,
24 pump input,
25 aspiration pump bypass line
26 aspiration pump,
28 pump output,
30 waste fluid receptacle,
48 user interface,
50 control module or CPU,
52 hand piece power driver,
53 irrigant pressure sensor,
54 infusion valve,
56 aspiration line vacuum sensor,
57 venting valve,
58 venting liquid deposit,
59 hand piece power cable,
60 hand piece power actuator,
64 waste fluid channel,
66 venting valve cable,
82 infusion valve cable,
84 irrigant pressure sensor cable,
86 aspiration pump control cable,
88 aspiration line vacuum sensor cable,
90 user interface cable,
94 miniature incision,
210 lensectomy surgical system,
270 occlusion valve,
272 occlusion valve cable,
274 actuator portion,
276 occlusion portion,
277 pinch valve,
278 collapsible elastic tubing segment,
280 in port,
282 out port,
284 plunger,
288 pivoting self-cleaning valve lid,
300 occlusion-break sensor,
310 occlusion-break sensor cable,
320 load cell,
330 collapsible elastic tubing segment,
335 diaphragm,
400 valve-and-sensor fixture,
410 valve-and-sensor fixture lid,
420 tubing guides,
425 lid latch

DETAILED DESCRIPTION OF THE INVENTION

Figure 1:
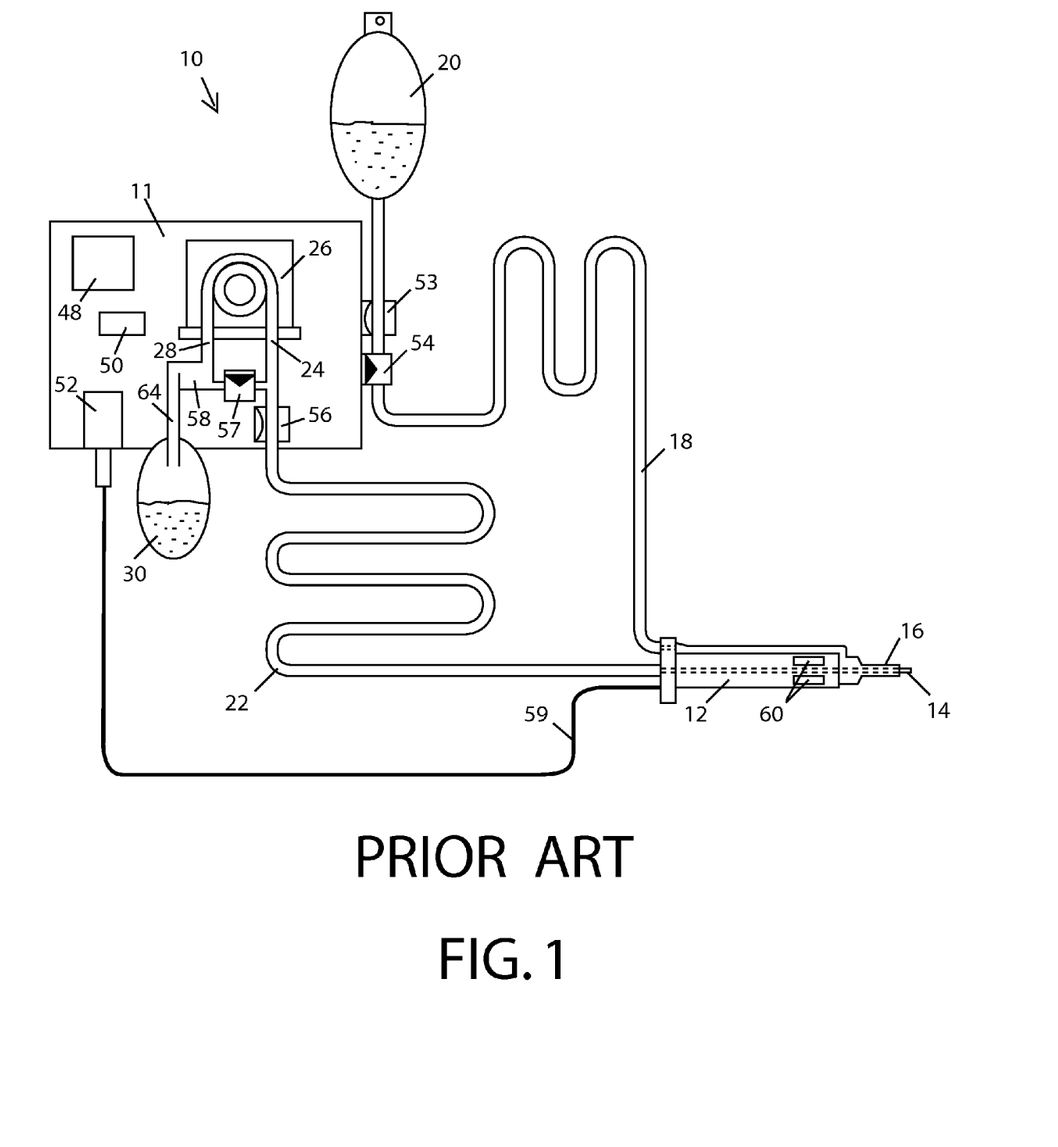
FIG. 1 is an illustration of a typical prior art lensectomy system.
Figure 4:
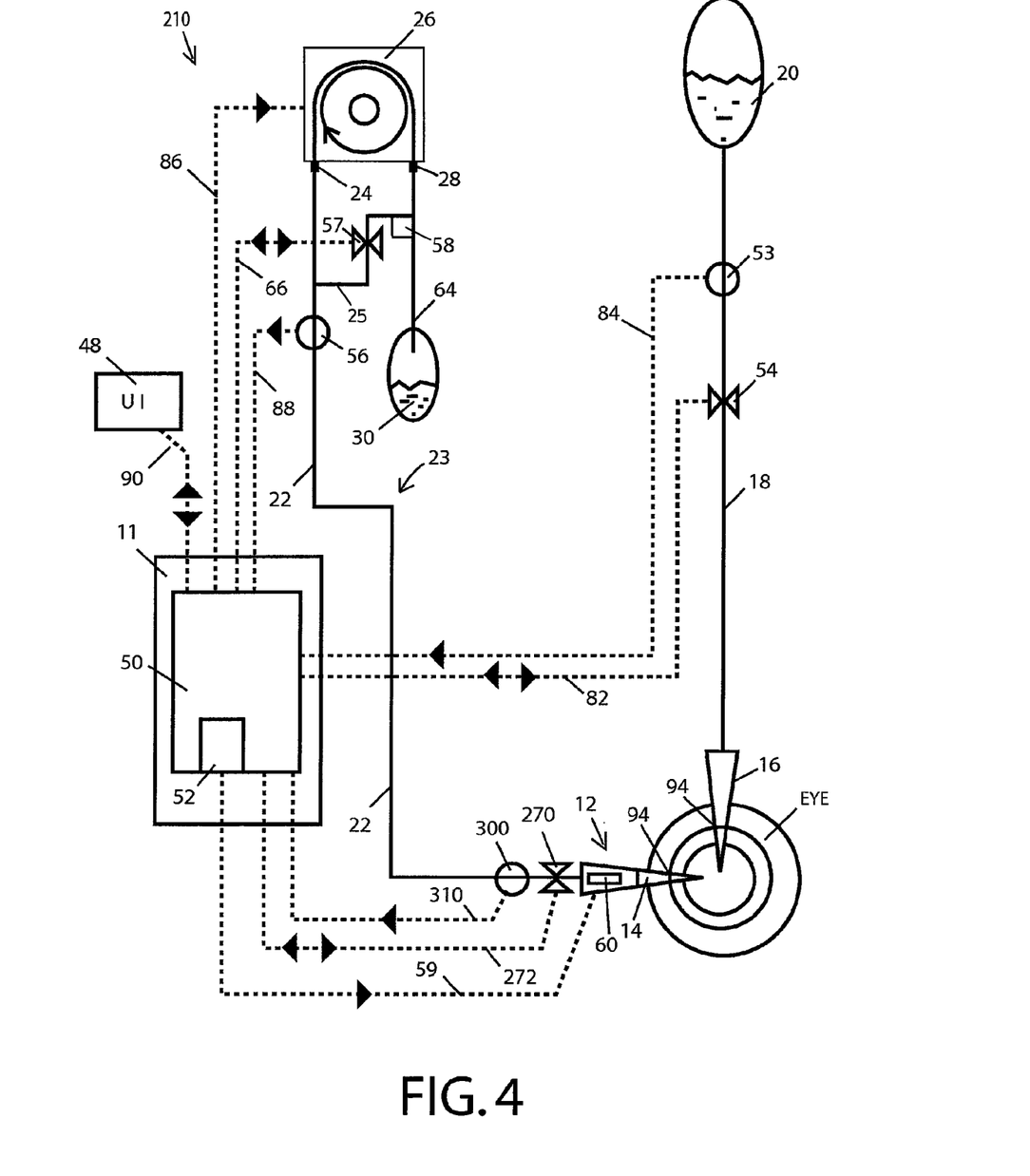
FIG. 4 is a schematic illustration of the preferred embodiment of the present invention.

As shown in FIGS. 1 and 4, in a prior art lensectomy surgical system 10 for use through an operating hand piece 12 includes a console 11. Console 11 generally includes a control module or CPU 50 providing control means, an aspiration pump 26 connected to CPU 50 through a cable 86 and a hand piece power driver 52 connected to CPU 50 through a cable 59. An irrigant solution is contained in an infusion source 20 being fed into an eye chamber with a pressure typically set by gravity or a compressed gas source. Hollow probe 14 and infusion probe 16 typically operate inserted into an eye chamber through one or more tight incisions 94. An infusion valve 54 can deliver irrigant solution through an infusion line 18 and infusion probe 16 into the eye under operator command through a user interface 48 typically including a foot pedal. Infusion valve 54 is connected to CPU 50 through a cable 82. Cable 82 can also provide a valve 54 status signal back to control module 50.

An irrigant pressure sensor 53 is operably connected to irrigation line 18 at console 11 to inform control module 50 about pressure of the irrigant solution through a cable 84. Fluid and tissue fragments can be aspirated from inside the eye by a vacuum force produced by aspiration pump 26 which is in fluid communication with the eye chamber through an aspiration line 22, hand piece 12 and hollow lensectomy probe 14. Vacuum in aspiration line 22 is monitored by control module 50 using a vacuum sensor 56 connected through a cable 88 usually located at console 11.

Fluid is aspirated into pump 26 through a pump input 24 and exits pump 26 as waste fluid through a pump output 28 across a waste fluid channel 64 into a waste fluid receptacle 30. The aspiration system described above includes an aspiration path 23 conformed by the aspiration fluid channel determined in sequence through lensectomy probe 14, hand piece 12, aspiration line tubing 22 and pump input 24. Pump 26 is typically a peristaltic or Venturi pump. An operator can instruct CPU 50 through user interface 48 to activate a power driver 52 to apply power to power actuators 60 inside hand piece 12 through a power cable 59. The energized actuators 60 transmit energy to hollow probe 14 delivering a lens tissue disruptive energy to disrupt the lens tissue allowing aspiration through the distal opening of hollow probe 14.

A venting liquid deposit 58 holds irrigant derived from pump output 28 that can serve as a source of venting fluid for a venting valve 57 actuated by control module 50 through a cable 66. Cable 66 can also provide a valve 57 status signal back to control module 50. Valve 57 provides aspiration line vacuum relieving means usually opening temporarily to relieve eventual vacuum inside aspiration path 23 after cycles of aspiration.

Deposit 58 is typically at atmospheric pressure but a pressurized source of venting fluid, preferably liquid, can also be implemented. User interface 48 operation typically includes a sequence of at least four distinctive command positions usually using a foot pedal as the input device. Position 0 is idle, 1 is only irrigation delivered to the eye, 2 is irrigation and aspiration, 3 is irrigation, aspiration and disruptive energy applied to tissues through hollow probe 14 inside the eye. Prior art system 10 may be a commercially available surgical console such as the Infiniti Surgical System from Alcon Laboratories, USA. Control module or CPU 50 may be any suitable microprocessor, micro-controller, computer or signal processor. Control module or CPU 50 exchanges data signals with user interface 48 through connector 90.

Figure 2:
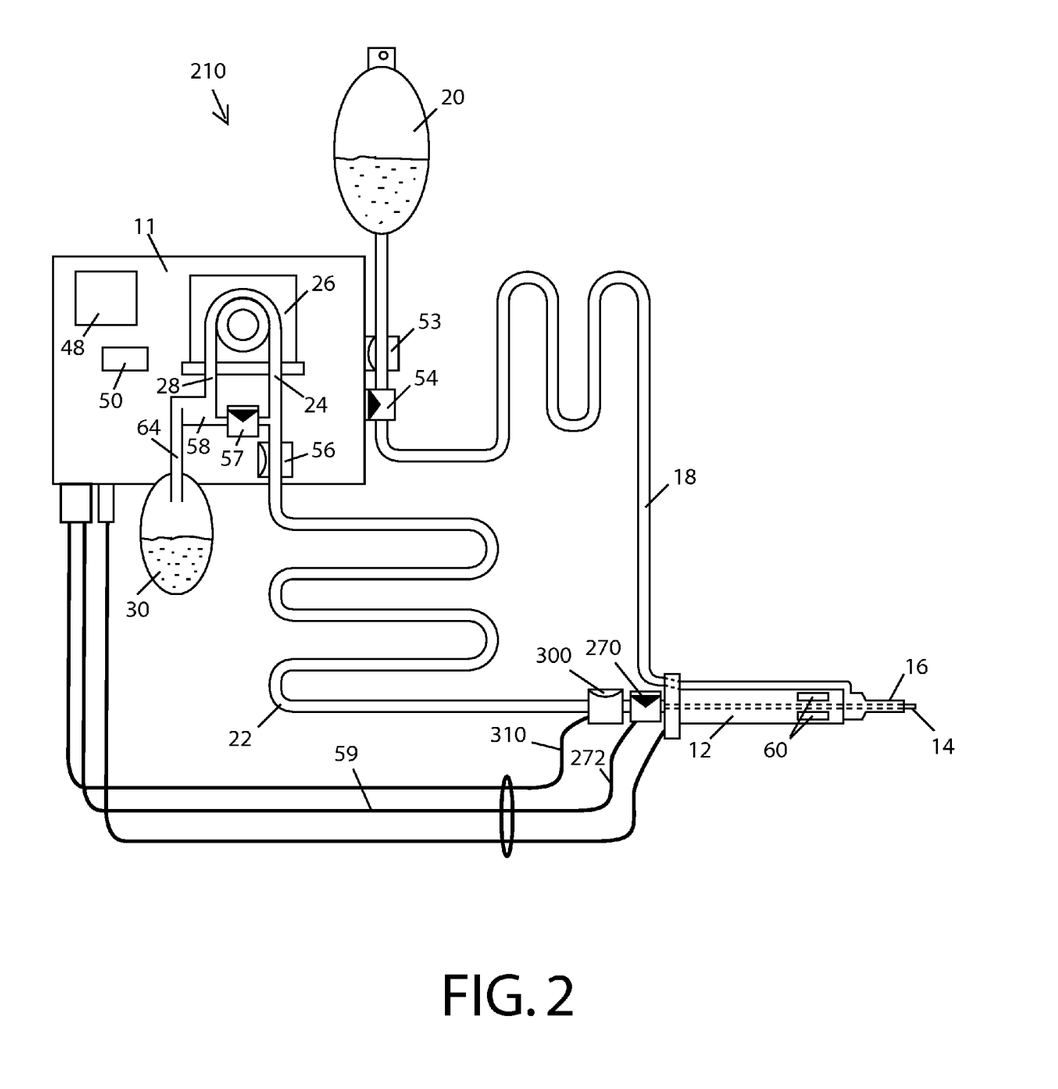
FIG. 2 is an illustration of one embodiment of the lensectomy system of the present invention.

The post-occlusion chamber collapse canceling system for a surgical apparatus of the present invention incorporates the elements described above for the prior art system illustrated in FIG. 1 Now turning to FIGS. 2 and 4, the post-occlusion chamber collapse canceling system of the present invention further incorporates a) an occlusion valve 270 that provides aspiration line occluding means and b) an occlusion-break sensor 300 that provides occlusion-break detecting means. Occlusion valve 270 receives commands from control module 50 through a cable 272. Cable 272 can also provide a valve 270 status signal back to control module 50 for safe operation. It can have an actuator portion 274 and an occlusion portion 276. For maximum efficiency, occlusion valve 270 should be located at the distal end of aspiration path 23, as near as possible to the eye. For practical reasons, valve 270 can be installed at the distal end of aspiration line 22, in proximity to hand piece 12 or inside hand piece 12. A preferred embodiment is considered where occlusion valve 270 is split, having actuator portion 274 attached to or incorporated in hand piece 12 and having occlusion portion 276 as part of the distal end of aspiration line 22. In this configuration, functionality of occlusion valve 270 is achieved when aspiration line 22 is connected to hand piece 12 by a detachable connector 21. This embodiment is advantageous because it allows having a disposable low cost occlusion portion 276 operating in combination with a non-disposable actuator portion 274.

Figure 6A:
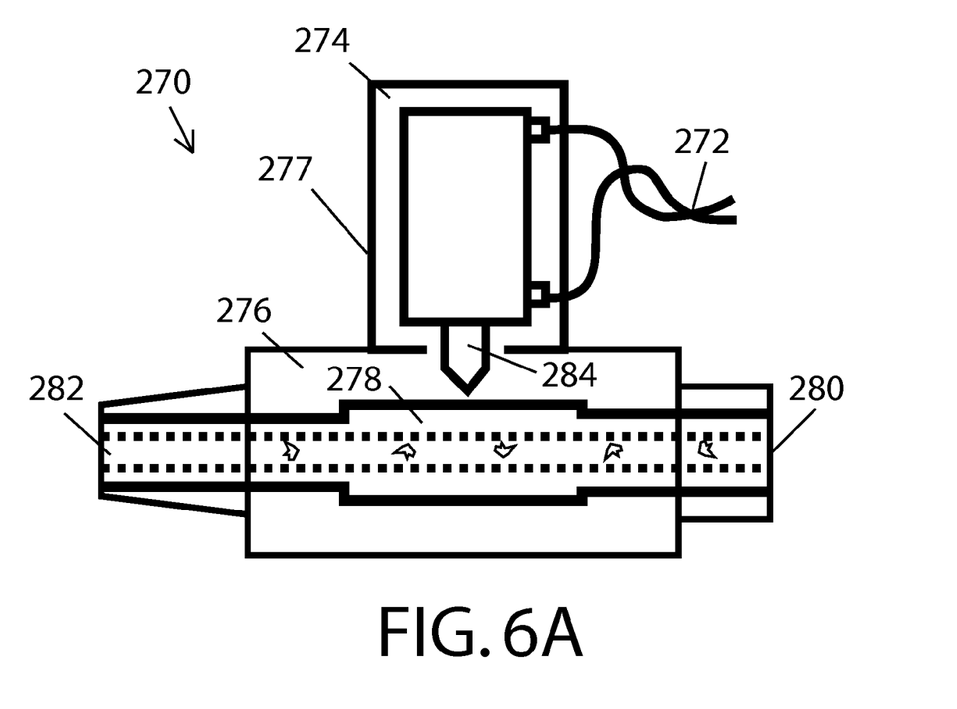
FIG. 6A is an illustration of one embodiment for an aspiration line blocking system corresponding to a pinch valve system shown in open condition.
Figure 6B:
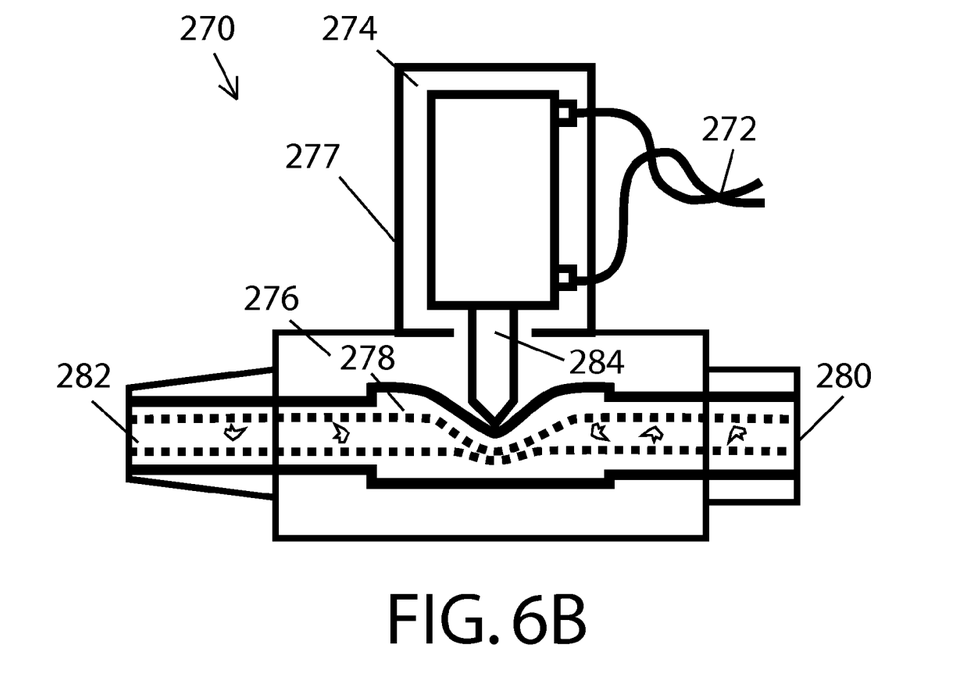
FIG. 6B is an illustration of the embodiment of FIG. 6A for an aspiration line blocking system shown in closed condition.

FIG. 6A depicts occlusion valve 270 in the form of a pinch valve 277 shown in open condition. Plunger 284 is retracted allowing the lumen of collapsible elastic tubing segment 278 to remain patent. An in port 280 receives the irrigant solution together with tissue fragments aspirated from inside the eye. The fluid and solid particles traverse tubing 278 with negligible resistance and exit out port 282 toward aspiration pump 26. FIG. 6B depicts pinch valve 277 in closed condition. Plunger 284 is protracted closing the lumen of collapsible elastic tubing segment 278, blocking aspiration path 23. In this condition, fluid and solid particles cannot traverse tubing 278. On reopening, the pinch valve self cleans so there is no unwanted clogging produced by tissue fragments aspirated from the surgical site. In the event a non-self cleaning occlusion valve was selected, a particle retaining filter should be inserted upstream to avoid clogging. Pinch valve 277 is a suitable election for operating as occlusion valve 270 because of speed of operation (tens of millisecond), non-clogging operation with liquids containing solid particles (tissue fragments), bidirectional flow and reliability. Pinch valve 277 actuator portion 274 can be a solenoid, an electromagnet, a linear actuator, a piezoelectric actuator, a piezoelectric motor or any other power source capable of temporarily pinching a segment of collapsible elastic tubing 278. Considerations such as weight, speed, reliability, resistance to sterilization and cost can influence the selection of the kind of valve actuator 274 depending on particular implementations of this invention. Solenoid driven pinch valve Model 390-NO-12-330 from ASCO Scientific, USA serves as an example of a valve that can be used as occlusion valve 270 in the present invention. This valve is designed as a two way normally open pinch valve for a 1.6 mm inner diameter tubing. A pulse-and-hold feature can be incorporated in the driving electronics of the solenoid to reduce heat generation, allowing the selection of lighter and smaller coils for the task of pinching the elastic tubing.

A valve-and-sensor fixture 400 can be implemented to accommodate occlusion valve 270 in a way that tubing 278 can be removably attached, for example as part of a disposable tubing set. In general aspiration line 22 should be made of a flexible material with a low contraction index with applied internal vacuum to allow faster response time of the present invention. The segment of collapsible elastic tubing 278 introduced for operation of pinch valve 277 should have the smallest allowable length not to degrade performance. An 8 mm segment of silicone tubing with an inner diameter of 1.6 mm and outer diameter of 3.2 mm has operated well while practicing this invention. Other forms of occlusion valves can be considered.

Figure 7A:
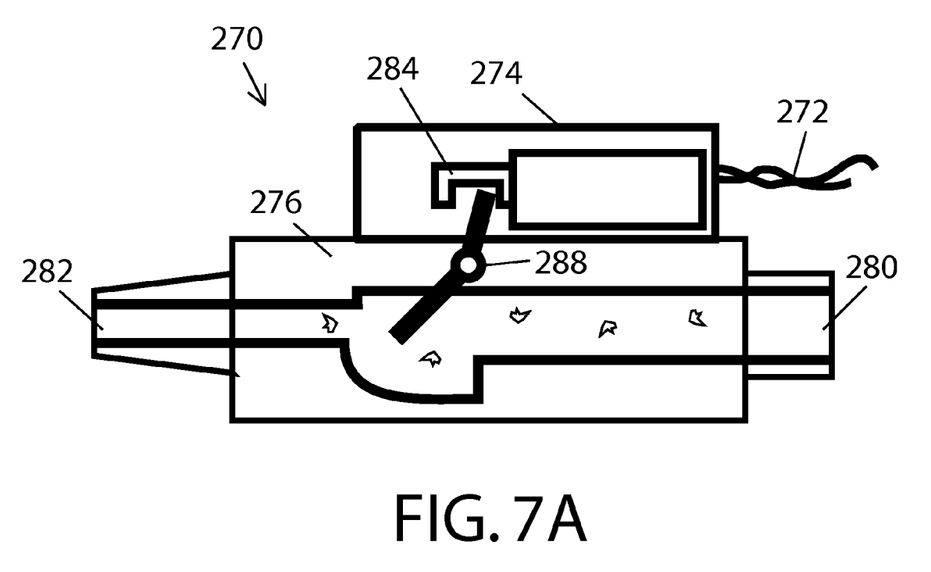
FIG. 7A is an illustration of another embodiment for an aspiration line blocking system shown in open condition.
Figure 7B:
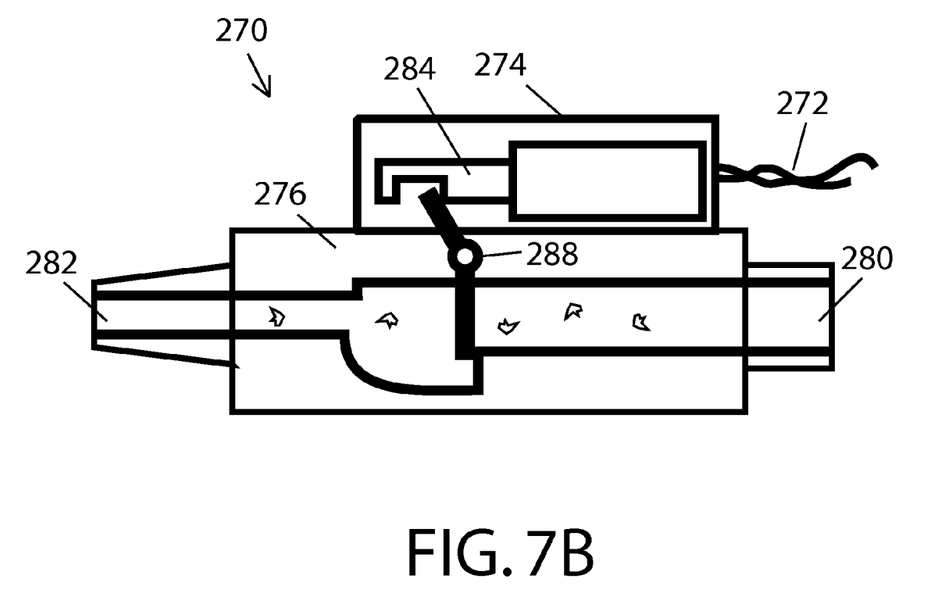
FIG. 7B is an illustration of the embodiment of FIG. 7A for an aspiration line blocking system shown in closed condition.

Depicted in FIGS. 7A and 7B is an alternative occlusion valve 270 shown in FIG. 7A in open position and in FIG. 7B in closed position. This occlusion valve has an input 280 and an output 282. An actuator portion 274 with solenoid 284 can be detachably coupled to operate pivoting lid 288 located in an eventually disposable occlusion portion 276 part of a tubing set. Design of the fluid path within valve 270 and of pivoting lid 288 avoids clogging by tissue fragments. Many other options exist to regulate flow besides the ON-OFF valves illustrated here, such as proportional valves also suitable for practicing this invention. Occlusion-break sensor 300 provides an electric signal to control module 50 through cable 310 indicating that an occlusion-break event has occurred. In a preferred embodiment, occlusion-break sensor 300 consists in a dP/dt sensor installed in the aspiration system.

The principle of operation is based on the fact that after an occlusion-break event occurs, there is a rapid drop in vacuum in the aspiration system. The rate of change of pressure dP/dt provides information about the timing and about the prospective magnitude of the post occlusion surge being detected. Control module 50 can use the onset and the magnitude of the dP/dt signal provided by sensor 300 to compute the beginning and duration of the chamber collapse canceling response. The faster an occlusion-break event is detected, the faster the compensating actions can be started improving performance.

Figure 8:
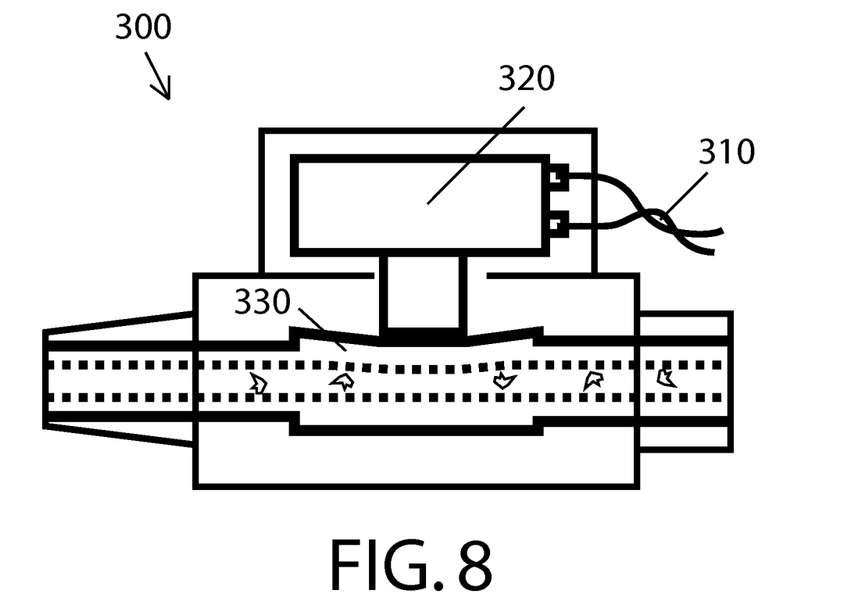
FIG. 8 is an illustration of one embodiment of an aspiration line occlusion-break sensing device operating by detecting force variations at the wall of tubing.
Figure 9:
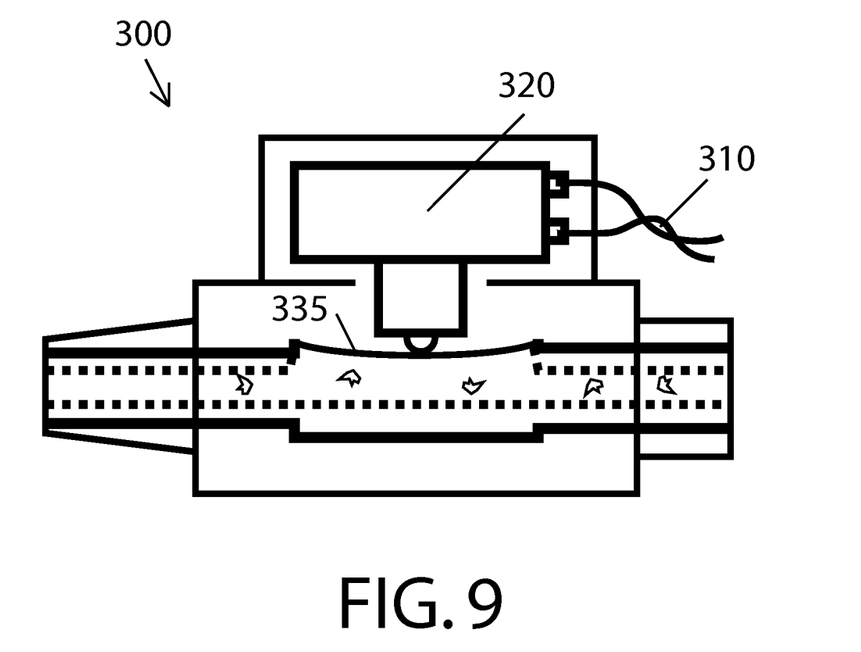
FIG. 9 is an illustration of another embodiment of an aspiration line occlusion-break sensing device that operates by detecting force variations in contact with a diaphragm.

Practicing this invention has taught that the location of sensor 300 is determinant in the delay observed between the actual occlusion-break and the detection signal provided by sensor 300. When using a dP/dt sensor as sensor 300 installed in aspiration path 23, the response time increases with increasing distance between the site of occlusion-break and sensor 300 location. Installing occlusion-break sensor 300 inside hand piece 12 or at the distal portion of aspiration line 22 rendered optimum results. In a preferred embodiment shown in FIG. 8, occlusion-break detector 300 uses a load cell 320 and tubing 330, and operates to provide a dP/dt signal. Load cell ELMF-B1-25N from Measurement Specialties, USA serves as an example of a load cell suitable for practicing this invention.

Figure 10A:
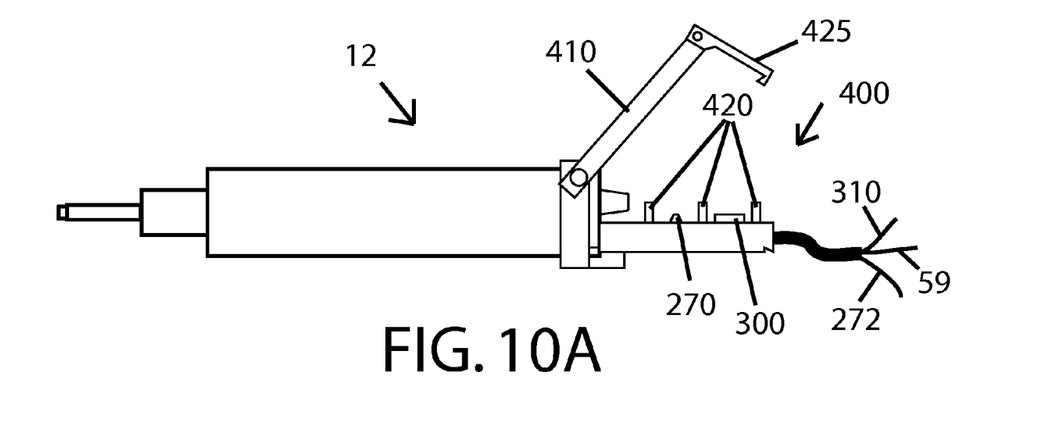
FIG. 10A illustrates a side view of a fixture that can hold an aspiration line blocking system and an aspiration line occlusion-break sensing device shown with the lid open and tubing detached.
Figure 10B:
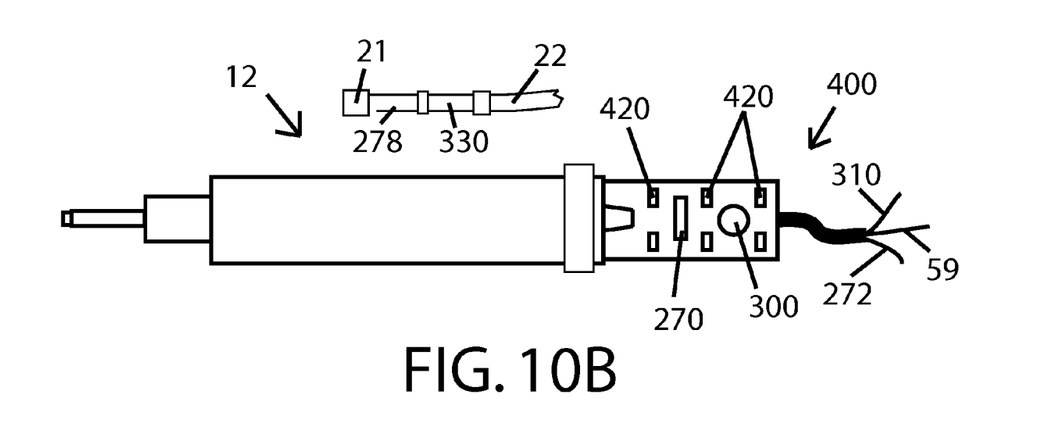
FIG. 10B illustrates a top view of the fixture from FIG. 9A shown here with the lid removed and tubing detached.
Figure 10C:
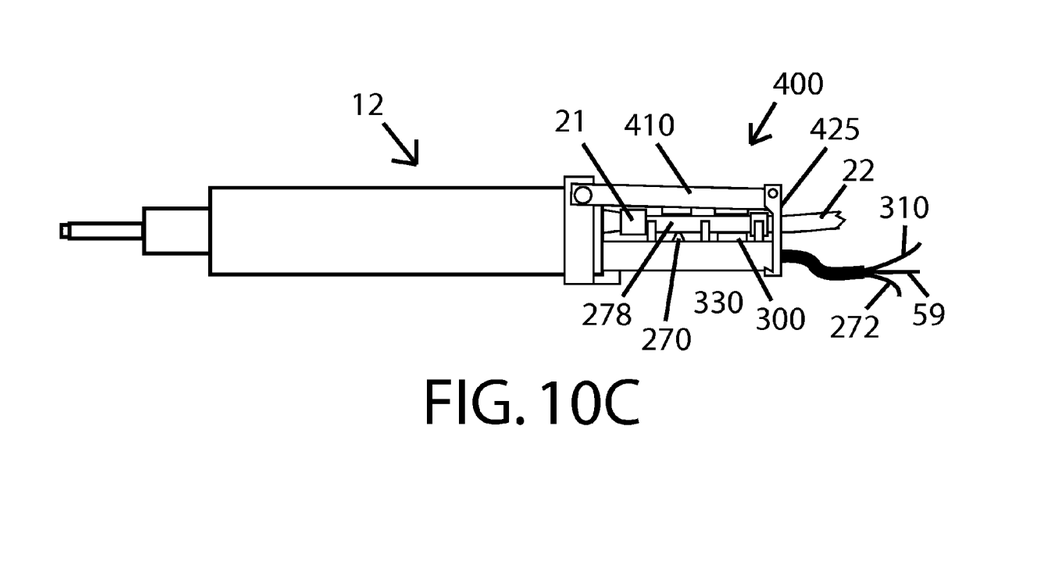
FIG. 10C illustrates a side view of the fixture from FIG. 9A shown here with the lid closed and tubing attached ready for operation.

Shown in FIGS. 10, 10B and 10C is a valve-and-sensor fixture 400 that can include sensor 300 in the form of load cell 320 about perpendicularly adjusted and slightly compressing the walls of a segment of elastic collapsible tubing 330 inserted near the distal end of aspiration path 23. Fixture 400 can have a hinged lid 410 incorporating a locking latch 425 and tubing guides 420. In this way tubing portions 278 and 330 together with aspiration line 22 distal connector 21 can be detachably coupled to hand piece 12.

Fixture 400 can be a stand alone unit or it can be integrated to a surgical hand piece 12. Collapsible tubing 330 is selected to preserve a patent fluid channel and remain in effective contact with load cell 320 across the full range of vacuum levels produced by aspiration pump 26. The minimum possible inner diameter of tubing 330 should preferably be above 1.5 mm to avoid clogging by solid particles. A silicone tubing segment of about 8 mm having 3.2 mm ID and 4.8 mm OD has shown to be operative for practicing this invention. Fluctuations in pressure inside the lumen of tubing 330 typical of occlusion-break produce an expansion of the walls of tubing segment 330 exerting a force over load cell 320 that is a function of vacuum at that location. Load cell 320 produces an electrical signal that is proportional to the force detected from tubing 330 walls. This signal is transmitted across cable 310 to control module 50 for processing.

One advantage of using this load cell and elastic tubing approach for occlusion-break sensor 300 is that the more expensive load cell can be integrated into a non disposable element fixture 400 or hand piece 12, while the inexpensive elastic tubing can be integrated into a disposable tubing set. Alternatively to tubing segment 330 and for improved performance, a differentiated portion including an elastic element such as a chamber with elastic walls can be designed to get in contact with load cell 320 such as a bellows region or a diaphragm region to transmit a force to load cell 320 that is a function of the vacuum in aspiration path 23.

In general terms, sensor 300 must be accurate to detect the timing of the occlusion break event, but not necessarily accurate to provide a proportional signal to dP/dt. This because aspiration line vacuum sensor 56 is typically well calibrated and can complement vacuum information to control module 50. Other kinds of sensors capable of timely detecting the occlusion break events can be used, such as vacuum sensors, pressure sensors, position sensors, acceleration sensors, thermal dilution flow sensors, ultrasonic flow sensors. These sensors could also be installed in the distal portion of aspiration path 23 to operate as occlusion-break detector 300, the output signal being converted to an estimated dP/dt value using electronic or digital differentiating means.

Alternatively, occlusion sensor 300 could only provide a digital ON-OFF output signaling the occurrence of an occlusion break to control module 50, and the vacuum at occlusion break onset information can be extracted from aspiration line vacuum sensor 56. Occlusion-break events also propagate a pressure wave upstream into irrigation line 18. For this reason sensor 300 in the form of a dP/dt sensor could be installed in irrigation line 18 although this approach proved less reliable and with increased response time.

OPERATION OF THE INVENTION

During a typical lensectomy procedure, an operator introduces irrigation and aspiration probes 16 and 14 inside the eye through one small incision 94. Alternatively, irrigation and aspiration probes 16 and 14 can also be introduced through separate incisions. The cataractous lens of the eye can be divided into fragments. The tip of lensectomy probe 14 is put in contact with the lens tissue and lens disrupting power can be applied typically in the form of ultrasonic vibration of the probe tip. Sometimes, the lens tissue can be removed by vacuum only. Setting console 11 foot pedal in positions 2 or 3 makes control module 50 to command having venting valve 57 closed, infusion valve 54 open and aspiration pump 26 operating up to a preset vacuum limit. With foot pedal in positions 2 or 3, when a lens fragment occludes the lensectomy probe tip, flow in the aspiration path 23 drops and vacuum can increase up to the maximum preset level.

In prior art systems, clearing of the probe tip from lens fragments allows fluid to escape the eye through aspiration path 23 at a rate faster than the rate at which irrigation probe 16 can replenish the eye, resulting in a chamber collapse caused by the post occlusion surge. Practicing the present invention, when occlusion-breaks at lensectomy probe 14 distal end, occlusion-break sensor 300 detects the onset and eventually also the magnitude for example of a vacuum drop in aspiration path 23, by providing a dP/dt signal to control console 50. On arrival of this signal reporting that an occlusion-break event has occurred, control module 50 can start an occlusion-break control response. This response can consist in the following actions:

1) Commanding temporary closure of occlusion valve 270 by delivering at least one closing signal. Closure of occlusion valve 270 blocks the passage between hollow lensectomy probe 14 and aspiration line 22, stopping any fluid and particles from further escaping the eye through aspiration path 23. This action cancels the surge flowing out of the eye. Occlusion valve 270 should be fast operating, ideally with a response time below 40 milliseconds both for opening and closure for improved performance.

2) About simultaneous with closure of occlusion valve 270 (action 1), control module also commands the temporary opening of venting valve 57, allowing free flow of liquid through aspiration pump bypass line 25 between venting liquid deposit 58 and aspiration path 23. After closure of the fluid communication between the eye chamber and aspiration path 23 by occlusion valve 270 (action 1), aspiration path 23 proximal to valve 270 can retain an unrelieved negative pressure. Opening venting valve 57 (action 2) produces a rapid cancellation of this negative pressure by allowing a volume of fluid to displace by pressure gradient from venting liquid deposit 58, across aspiration pump bypass line 25, into aspiration line path 23. This flow terminates when the pressure difference across valve 57 equalizes. Venting valve 57 should be fast operating, ideally with a response time below 40 milliseconds both for opening and closure for improved performance. Operation of aspiration pump 26 can be modified by control module 50 for about the duration of occlusion valve 270 closure to expedite the vacuum cancellation effect of venting valve 57. This modification can consist in a slow down, detent or even reverse operation. After ending of the occlusion and venting actions, the speed of pump 26 can be transitorily increased above normal for enhanced performance.

3) Control module 50 determines an optimal duration for the activation signals delivered to occlusion valve 270 and venting valve 57 (actions 1 and 2). These signals should be of the minimum effective duration in a way that chamber collapses are effectively cancelled while still allowing the system to resume normal operation rapidly. Control module can deliver fixed duration driving signals for valves 270 and 57. Alternatively, control module 50 can compute the duration of driving signals for valves 270 and 57 for improved performance, using for example the vacuum present at the onset of the occlusion break. As a mode of example, an algorithm that proved efficient to compute the duration of the driving signal for valves 270 and 57 in a particular setting was the following:

IF dP/dt>+800 mmHg/sec THEN Pulse Duration=300+(Vacuum at break onset*0.8) milliseconds ELSE no blocking-venting action performed.

Finally, control module 50 can use a feedback loop to operate valves 270 and 57 until a determined level of vacuum in aspiration path 23 is achieved. The onset and duration of the driving signal for valves 270 and 57 can be synchronous or not. For computation of the optimal duration of these signals for effective pressure equalization, control module 50 can take into consideration factors such as lensectomy probe 14 resistance to flow, aspiration line 22 elastic properties, vacuum level at the onset of the occlusion-break provided by aspiration line vacuum sensor 56 or sensor 300 (when available), rate of change of vacuum during the occlusion-break event (dP/dt), aspiration flow rate, irrigation pressure at eye level, resistance to flow of irrigation path including resistance of infusion probe 16, wound size among others. Practice of the present invention using an Infiniti Console™, an Intrepid Cassette™, a 0.9 mm tapered Micro-Tip™ and an Ultra-Sleeve™ (all from Alcon Laboratories, USA.) has taught that when using actuator signals of similar duration for occlusion valve 270 closure and for venting valve 57 opening, the optimal duration of these pulses ranged between 100 milliseconds and 800 milliseconds depending on aspiration path 23 vacuum at the onset of the occlusion-break. Duration of actuator 270 and 57 driving signals had to be increased with increasing occlusion-break onset vacuum levels for proper chamber collapse control. Control module 50 can determine the optimal pulse duration for a given occlusion-break situation by using a pre-built look-up table stored in ROM. Alternatively a pre-built formula incorporating a set of the aforementioned parameters can be used. Also, a servo loop can be used to terminate the chamber collapse canceling actions 1 and 2 by monitoring the signals from aspiration line vacuum sensor 56 and/or from occlusion-break sensor 300 in real time. Once the signals coming from these sensors tell control module 50 that vacuum inside aspiration path 23 has reversed back to desirable levels, actions 1 and 2 can be terminated. Beginning and termination of actions 1 and 2 can occur simultaneously or not, depending of the chamber collapse suppressing algorithm used by control module 50.

4) An optional action can consist in having control module 50 deliver an inhibit signal to hand piece power driver 57 in a way that the lens disrupting power delivered by lensectomy probe 14 is reduced to safe levels during the programmed occlusion and venting. This action may be of particular importance with ultrasonically operated lensectomy probes 14 to avoid wound thermal injuries caused by lack of effective cooling during the programmed occlusion.

In an alternative embodiment, the vacuum relieving action 2 can instead be performed by reverse operation of aspiration pump 26. Speed and duration of this reverse operation may be controlled by control module 50 using a predetermined formula or a servo mechanism based on vacuum sensor 56 and/or detector 300 readings.

In another alternative embodiment, the vacuum relieving action 2 performed by venting valve 57 can be performed using pressurized fluid. Also normally closed valve 57 and normally open valve 270 can be replaced by a single three way pinch valve to simultaneously perform the actions of venting and of aspiration line occlusion. This three way valve modality can be installed at the distal portion of the aspiration path 23 for better performance.

When using irrigation line 18 as the source of the pressurized fluid, practice of this embodiment showed a reduced performance due to less fluid available to refill the eye chamber in the post occlusion-break period.

Figure 3:
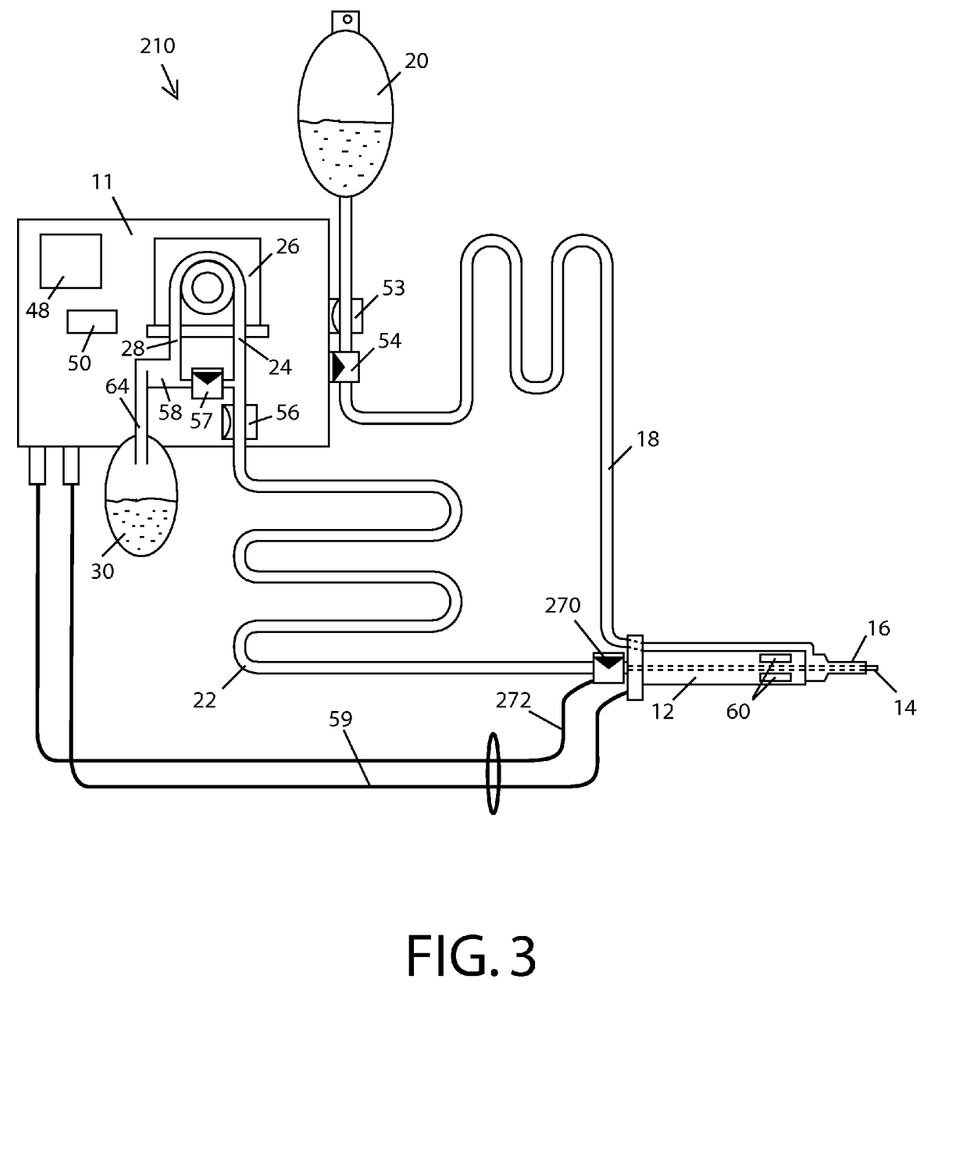
FIG. 3 is an illustration of another embodiment of the lensectomy system of the present invention.
Figure 5:
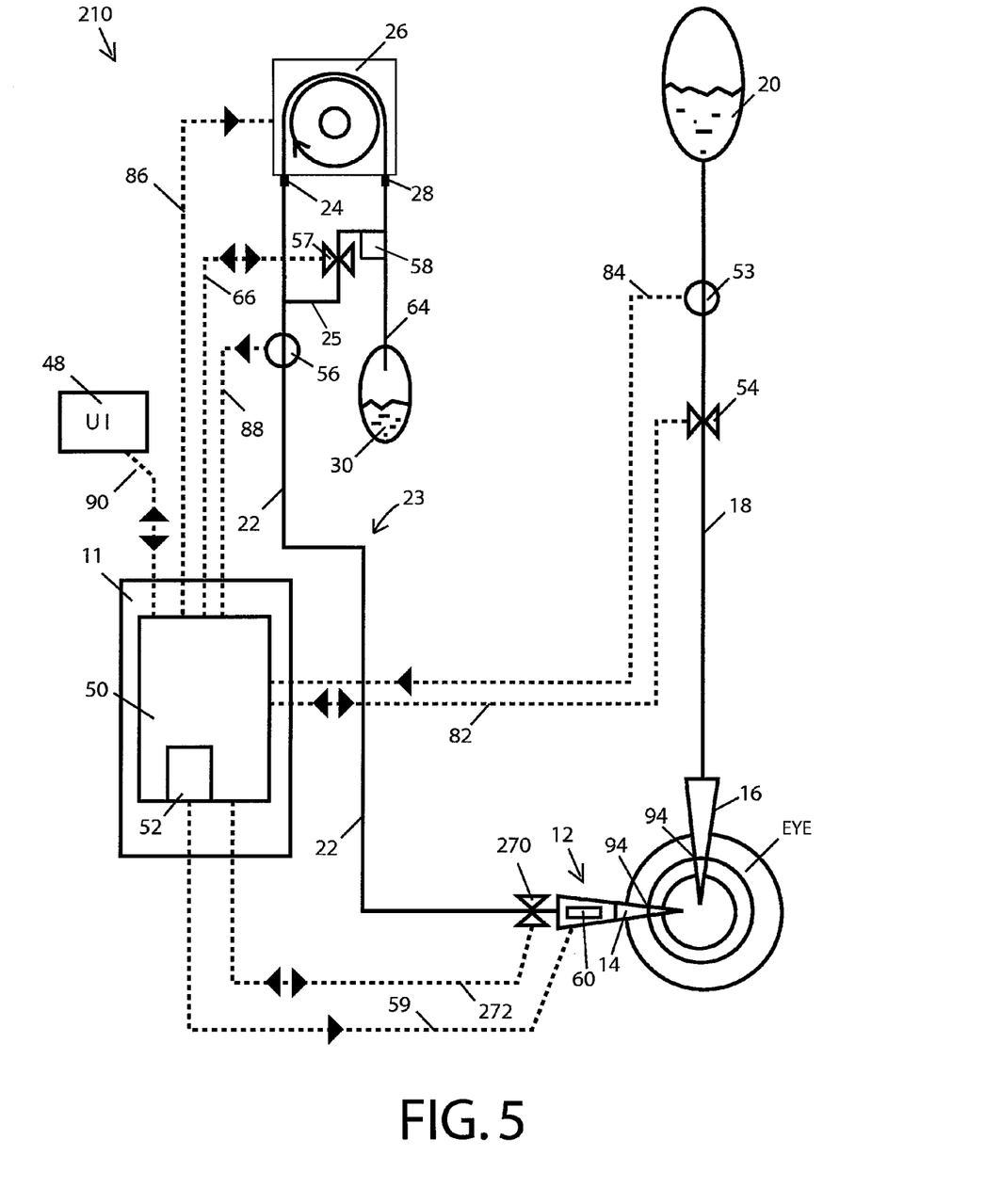
FIG. 5 is a schematic illustration of an alternative embodiment of the present invention.

In an alternative embodiment depicted in FIGS. 3 and 5, the function of occlusion-break sensor 300 located distally in aspiration path 23 is replaced by aspiration line vacuum sensor 56 typically located at console 11. A dP/dt value is derived from sensor 56 readings to trigger the post occlusion surge response from control module 50. The duration of the occlusion and venting intervals can be fixed, computed of controlled by a feedback loop including sensor 56 or 300. In a preferred embodiment, control module 50 uses a look-up table stored in ROM or a pre-built formula.

Figure 11:
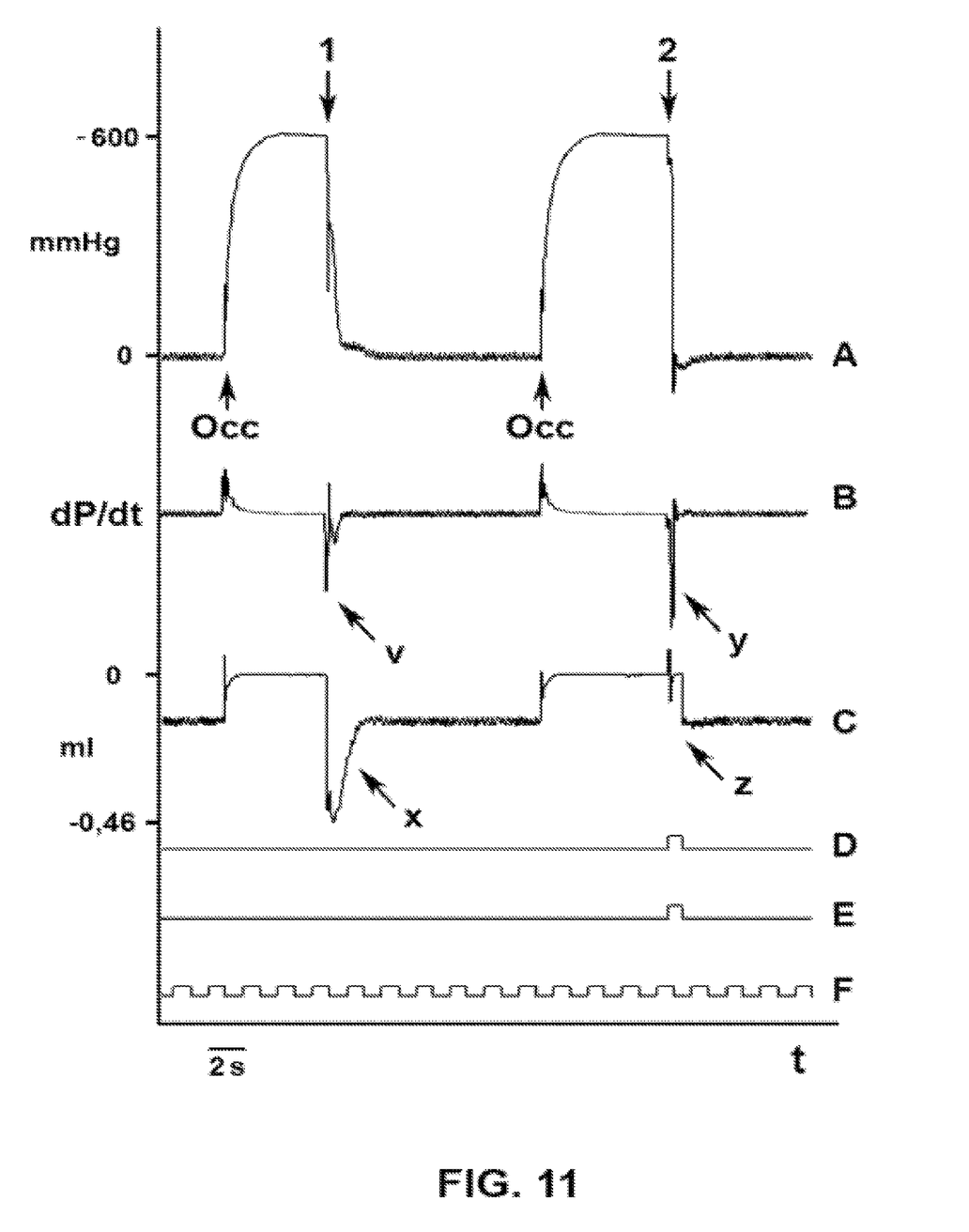
FIG. 11 is a chart recording depicting aspiration line vacuum, dP/dt and chamber collapse volume with (right) and without (left) the incorporation of the post-occlusion chamber collapse canceling system of the present invention.

FIG. 11 is a chart recording to demonstrate the advantage of practicing the present invention by comparing post occlusion chamber collapse with and without operation of the system. This recording was made using an Infiniti console, a non-ABS tapered microtip, irrigant pressure set to 90 cmH2O and an Intrepid fluidics cassette (Alcon, USA). Tracing in A corresponds to aspiration line vacuum. B is the pressure differential, C is eye chamber volume, D is occlusion valve 270 activation signal, E is venting valve 57 activation signal. The left portion of the tracing depicts the relevant occlusion and post occlusion events in a surgical system of the prior art. The arrow pointing up labeled Occ signals the start of an occlusion with vacuum rising up to 600 mmHg. The arrow pointing down labeled 1 signals the moment of occlusion-break. Aspiration line vacuum rapidly drops at a rate typically above 1500 mmHg/sec depicted in trace B (arrow v) translating into the chamber collapse seen in trace C (arrow x). Now turning to the right side of the chart recording, tracings from a surgical system incorporating the present invention are illustrated. The arrow pointing up labeled Occ signals the start of an occlusion event with vacuum rising to 600 mmHg in the aspiration line. The arrow pointing down labeled 2 signals the moment of occlusion-break. A peak of dP/dt shown in trace B (arrow y) is analyzed by control module 50 delivering an occlusion signal shown in D for occlusion valve 270 and a venting signal shown in E for venting valve 270. The computed value for the duration of these signals is 780 milliseconds. As can be observed in the right side of trace C (arrow z), there is virtually no evidence of chamber collapse as a consequence of occlusion-break with the implementation of the present invention.

CONCLUSION, RAMIFICATIONS AND SCOPE OF THE INVENTION

Thus, the reader will see that the post-occlusion chamber collapse canceling system of the present invention provides an effective and reliable improvement over the prior art allowing to perform lensectomy procedures with high vacuum levels through smaller incisions. This feature leads to more efficient surgical procedures. While the above description contains many specificities, these should not be construed as limitations on the scope of this invention but rather as an exemplification of the preferred embodiment thereof. In fact, the preferred embodiment has been selected aimed to provide optimum performance at the reduced cost required for disposable surgical consumables. Many other variations are possible. For example venting valve 57 can be any kind of valve. This valve can be an ON/OFF valve or a proportional valve and may be located in other position than console level. Aspiration line occlusion valve 270 can be any kind of ON/OFF valve or a proportional valve, such as a needle valve, acting in cooperation with a solid particles retaining filter to avoid clogging. Although valve 270 performs best when located at the distal end of aspiration path 23 near hollow probe 14, it can be located at other position between probe 14 and pump 26, assuming a compromise in performance. A similar consideration can be made for occlusion-break sensor 300 regarding location.

Although this invention has been designed for use in ophthalmic surgery, other surgical procedures performed inside collapsible body chambers may benefit from its implementation.

Accordingly, the scope of the invention should be determined not by the embodiments illustrated, but by the appended claims and their legal equivalents.

The invention claimed is:

1. A pressure surge cancelling device comprising:
a fixture comprising a hinged lid and a support structure, the hinged lid having a hinge end and a latch end, and a locking latch located on the latch end of the hinged lid;
a surgical hand piece having an end fixed to the fixture, the end having an aspiration port, the hinge end of the hinged lid coupled to the surgical hand piece;
a length of aspiration tubing insertable into and removable from the fixture between the support structure and the hinged lid, the length of aspiration tubing terminating in a distal connector, the distal connector removably coupled to the aspiration port, the length of aspiration tubing having a first segment and a second segment;
a sensor located on the support structure of the fixture such that the second segment of the length of aspiration tubing is adjacent to the sensor when the length of aspiration tubing is inserted into the fixture, the sensor for detecting a pressure in the aspiration tubing;
a pinch valve coupled to the support structure of the fixture such that the first segment of the length of aspiration tubing is adjacent to the pinch valve when the length of aspiration tubing is inserted into the fixture;
the first segment of the length of aspiration tubing having a first length and a first outer diameter; and
the second segment of the length of aspiration tubing having a second length and a second outer diameter;
wherein the first outer diameter is different from the second outer diameter.

2. The device of claim 1 wherein the sensor is located adjacent to the valve.

3. The device of claim 2 further comprising:
a plurality of tubing guides located on the fixture.

4. The device of claim 3 wherein the plurality of tubing guides center the length of aspiration tubing over the sensor and the valve.

5. The device of claim 1 further comprising:
a controller electrically coupled to the sensor such that the controller receives a signal from the sensor, the signal indicating a pressure in the length of aspiration tubing.

6. The device of claim 5 wherein the controller is operable to direct the valve to be closed based on the signal received from the sensor.

7. The device of claim 1 wherein the first segment of the length of aspiration tubing is adapted for use with the pinch valve.

8. The device of claim 7 wherein the first outer diameter of the first segment of the length of aspiration tubing is about 3.2 millimeters.

9. The device of claim 1 wherein the second segment of the length of aspiration tubing is adapted for use with the sensor.

10. The device of claim 9 wherein the second outer diameter of the second segment of the length of aspiration tubing is about 4.8 millimeters.

11. The device of claim 1 wherein the first outer diameter is less than the second outer diameter.

* * * * *